United States Patent [19]

Williams

[11] Patent Number: 4,735,202

[45] Date of Patent: Apr. 5, 1988

[54] MICROSURGICAL KNIFE WITH LOCKING BLADE GUARD

[75] Inventor: Rodger W. Williams, Nashville, Tenn.

[73] Assignee: Alcon Laboratories, Inc., Fort Worth, Tex.

[21] Appl. No.: 916,422

[22] Filed: Oct. 6, 1986

[51] Int. Cl.⁴ ............................................. A61B 17/32
[52] U.S. Cl. ...................................... 128/305; 30/162; 30/295
[58] Field of Search ...................... 128/305, 305.3, 314, 128/315, 329 R, 329 A; 30/143, 151, 162, 163, 293; 401/117; 604/192, 198, 263, 172

[56] References Cited

U.S. PATENT DOCUMENTS

| | | | |
|---|---|---|---|
| 3,169,527 | 5/1965 | Sheridan | 604/172 |
| 3,706,106 | 12/1972 | Leopoldi | 7/14.1 |
| 3,905,101 | 9/1975 | Shepherd | 30/162 |
| 3,945,117 | 3/1976 | Beaver | 30/287 |
| 4,071,952 | 2/1978 | Meshulam et al. | 30/151 |
| 4,414,974 | 11/1983 | Dotson et al. | 128/305 |
| 4,425,120 | 1/1984 | Sampson et al. | 604/198 |
| 4,576,164 | 3/1986 | Richeson | 128/305 |

Primary Examiner—Dalton L. Truluck
Assistant Examiner—F. Wilkens
Attorney, Agent, or Firm—James A. Arno; Gregg C. Brown

[57] ABSTRACT

A disposable microsurgical knife having a blade guard that can be locked into a blade covering position and then easily removed from the knife body prior to introduction to the sterile field is disclosed. The blade guard includes a cylindrical sleeve having a longitudinal slot communicating with a forward open end thereof and terminating in a circumferential notch. The knife body includes a small locking tab formed adjacent a forward tapered portion of the knife. The blade guard is initially assembled on the knife by longitudinally sliding along the knife body from a rear end thereof until the locking tab enters the longitudinal slot assisted by a funnel-shaped leading end for ease of entry. In the blade covering position, simple rotation of the sleeve forces the locking tab into the circumferential notch. For easy removal, reverse rotation of the sleeve causes the tab to re-enter the slot whereupon the sleeve is removed from the knife by sliding rearwardly along the knife body.

8 Claims, 1 Drawing Sheet

U.S. Patent
Apr. 5, 1988
4,735,202
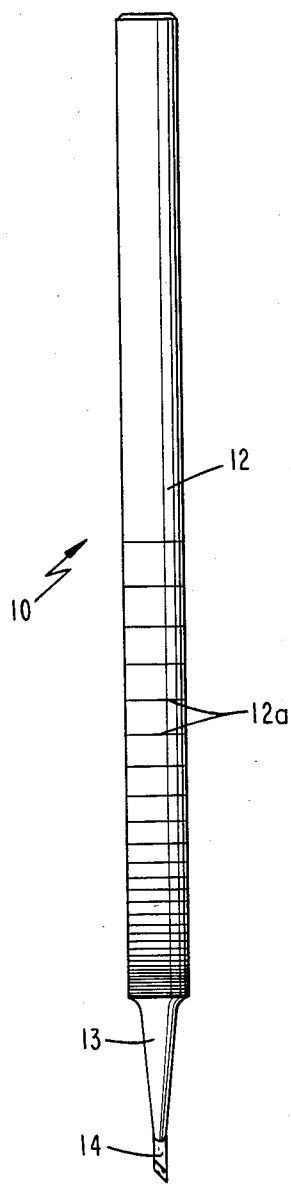
Fig. 1
(PRIOR ART)
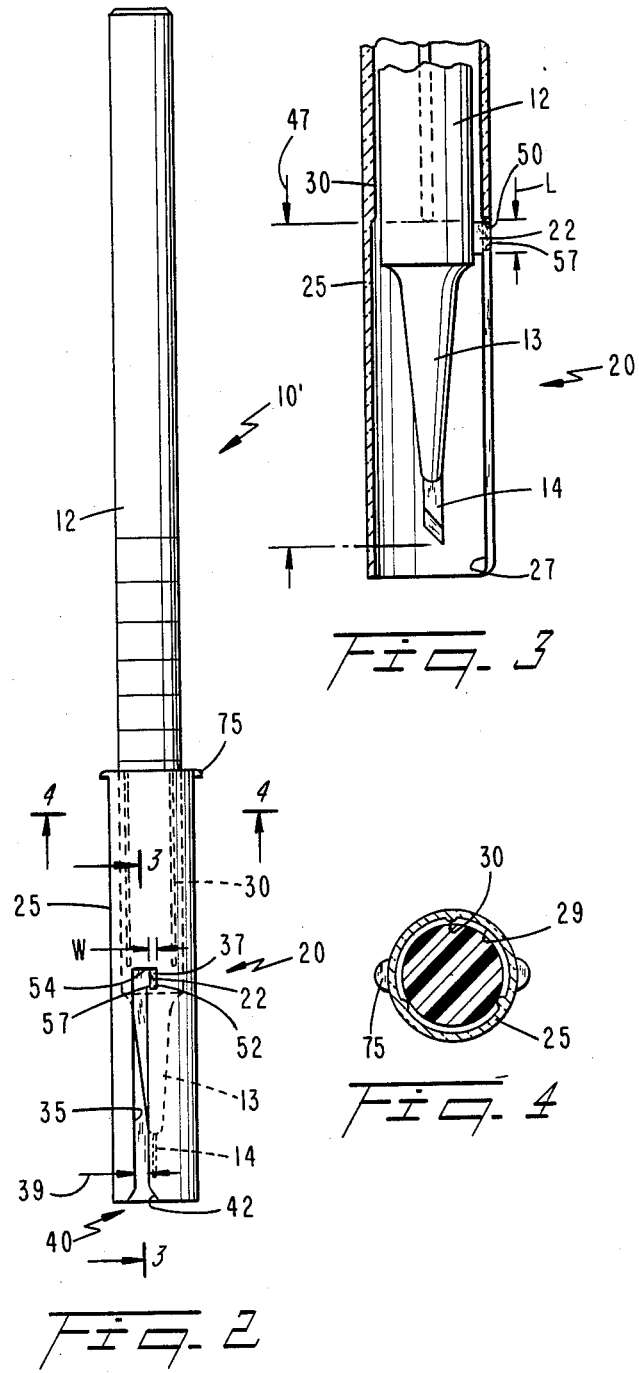

MICROSURGICAL KNIFE WITH LOCKING BLADE GUARD

TECHNICAL FIELD

The present invention relates generally to surgical knives, and more particularly to a disposable microsurgical knife having a movable blade guard for protecting the sterility and structural integrity of the knife blade from damage prior to introduction to a sterile field.

BACKGROUND ART

FIG. 1 is an illustrtion of a microsurgical knife 10 including a knife body 12 having a cutting blade 14 at one end thereof. More specifically, the knife body 12 includes a forward portion 13 that tapers downwardly towards blade 14 to provide good visibility of the cutting tip. The knife body 12 has a gripping surface 12a that may be knurled or otherwise roughened to provide a secure grip. Microsurgical knife 10 in disposable form is manufactured by the assignee of the present application. The microsurgical knives 10 are shipped in vacuum formed trays of the type disclosed in U.S patent application Ser. No. 739,217 filed May 30, 1985, assigned to the present assignee. Said vacuum formed tray is essentially of a type providing snapfitting securement between the knife body and portions of the tray. The knife is easily removed from the tray although securely and snugly held while in the tray and prior to introduction to the sterile field.

It has recently been discovered that knives 10 are occasionally being introduced to the sterile field with the knife blades 14 in a bent and therefore unsatisfactory condition. It is believed that the damage may occur when the knife 10 is removed from the vacuum formed tray for introduction to the sterile field. It is further suspected that such damage to the blade 14 occurs as the rear end of knife body 12 remote from blade 14 is manually lifted from the surface of the tray causing possible and undesirable bending contact between the knife blade and tray body.

In light of the above problem, it would be desirable to provide a structure for protecting the structural integrity of the cutting blade 14 until knife 10 is introduced to the sterile field. Such a structure should be simple to manufacture and therefore economical while requiring economy of effort in attachment and subsequent detachment from the knife body.

U.S. Pat. No. 4,576,164 to Richeson discloses a disposable microsurgical knife having a shroud that can be locked into a position protecting a blade located at one end of the knife body. The cylindrical shroud is in the form of a sheath that is movable axially along the knife body. The shroud is formed with a plurality of projections mating with a complex arrangement of longitudinal and circumferential grooves formed on the exterior surface of the knife body. This complicated arrangement of grooves on the knife body allows the shroud to be locked in two or three positions wherein in one position the shroud in fact acts as an enlarged centrally located handle which may discourage use of the knife by various surgeons. If the shroud were to be removed entirely from the knife body, the exposed system of complicated longitudinal and circumferential grooves may result in an inconvenient grip for the surgeon. Thus, the locking shroud disclosed in the aforesaid patent has many distinct disadvantages.

U.S. Pat. Nos. 3,706,106; 3,905,101; 3,945,117; and 4,414,974 disclose other types of surgical knives having movable blade protective structures.

It is accordingly one object of the present invention to provide a surgical knife having a removable guard for protecting the blade during shipping or otherwise prior to introduction to the sterile field.

It is another object of the present invention to provide a disposable microsurgical knife with a blade guard that is easily attached to entirely cover the cutting blade of the knife so that the blade will not be damaged in shipping and will remain in protective position until easy removable prior to introduction to the sterile field.

Still a further object is to provide a guard capable of easy yet positive locking engagement with the microsurgical knife body and which utilizes locking structure that does not interfere with the grip provided for the surgeon on the knife body when the guard is removed from the knife.

DISCLOSURE OF THE INVENTION

The present invention provides a disposable microsurgical knife having a movable blade guard in the form of a cylindrical sleeve being movable axially along the knife body, with locking means for selectively locking the sleeve in a position substantially entirely surrounding the cutting blade in spaced relation thereto. The sleeve projects forwardly from the knife blade located within the confines of the sleeve in the locking position. To provide locking of the guard sleeve in a blade covering position, there is provided at least one projection on one of the locking sleeve or knife body for engagement with a locking notch on the other of the sleeve or knife body.

Preferably, a single locking projection formed on the knife body adjacent the forward portion thereof is adopted to enter a longitudinal slot formed in the cylindrical sleeve. The slot extends from the forward opening of the sleeve where it has tapered walls for ease of locating the locking projection in the slot, and terminates within the intermediate portion of the sleeve where it is formed with a circumferentially extending notch. As the sleeve slides along the knife body after initial engagement by passing the rear end of the knife body through the forward opening of the sleeve, the locking projection contacts the back wall of the longitudinal slot. Slight rotation of the sleeve or knife body then forces the projection to enter the locking notch so that the sleeve is in a blade covering position.

One or more tabs may project outwardly from the exterior surface of the cylindrical sleeve to prevent the knife from rolling when on a Mayo stand. The sleeve may also be provided with one or more longitudinal ribs projectiong radially inward from the interior surface of the sleeve to promote easy sliding movement of the sleeve along the knife body.

Positive locking engagement between the locking projectin and circumferential notch may be obtained by dimensioning the projection so that it is of slightly greater length than the corresponding dimension of the locking notch in the longitudinal direction. Thus, positive locking contact is obtained by a wedging effect taking into account the normal yieldability of the plastic material of which the cylindrical locking sleeve is preferably formed.

The cylindrical sleeve forming the locking blade guard of the invention is designed for complete removal from the knife body when unlocked from the blade covering position. Thus, the conventional grip afforded the surgeon by the knife body is unaffected with the present invention. The feature of a single locking projection projecting radially outward from the knife body adjacent its forward portion has slight effect, if any, as to the convenient grip afforded the surgeon.

Additional objects, advantages and novel features of the invention will be set forth in part in the description which follows and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWING

FIG. 1 is a side elevational view of a conventional disposable microsurgical knife;

FIG. 2 is a side elevational view of a disposable microsurgical knife modified for use with the present invention in combination with a locking blade guard depicted in the blade covering locked position;

FIG. 3 is a sectional view taken along the line 3—3 of FIG. 2 depicting further structural detail of the locking mechanism of the invention; and FIG. 4 is a sectional view taken along the line 4—4 of FIG. 2 of other features of the invention.

BEST MODE FOR CARRYING OUT THE INVENTION

Microsurgical knife 10' used in the present invention in conjunction with locking blade guard 20 of the invention is virtually identical to microsurgical knife 10 depicted in FIG. 1 discussed above, with the addition of a small locking tab 22 formed on knife body 12 adjacent forward tapered portion 13. As best seen in FIG. 3, locking tab 22 is generally of rectangular cross-section and has its major dimension or length L extending in the longitudinal direction of the knife body. In the circumferential direction of the knife body, the thickness or width W is relatively small (i.e., tab 22 is thin). Locking tab 22 is nonetheless configured to provide positive locking contact for securing blade guard 20 in a blade covering position in the unique manner described below. When the guard 20 is removed from knife 10' to expose blade 14, locking tab 22 remains basically unobtrusive on the knife body to advantageously prevent interfering with the convenient grip for the surgeon normally provided on the outer surface of the knife body.

Blade guard 20 comprises a cylindrical sleeve 25 preferably formed of transparent plastic material having a forward opening 27 and a rear opening 29. The inner diameter of sleeve 25 is slightly greater than the corresponding outer diameter of knife body 12 so that the sleeve is easily mounted to the knife body preferably by inserting the rear end of the knife body into forward opening 27. One or more longitudinally extending ribs 30 formed on the inner surface of sleeve 25 and projecting radially inward a short extent may be provided to reduce friction and promote an easy sliding movement of the cylindrical sleeve along knife body 12.

Sleeve 25 includes a longitudinal slot 35 that communicates with forward opening 27 and that extends longitudinally through approximately one-half of sleeve 25 before terminating into a circumferentially extending locking notch 37. The width 39 of slot 35 is slightly greater than the corresponding width W of locking tab 22 to permit easy sliding movement of the tab through the longitudinal slot as blade guard 20 slides forwardly into blade covering position discussed infra. Longitudinal slot 35 is preferably of constant width 39 along substantially its entire length except for circumferential locking notch 37 formed at its terminal end within sleeve 25 and forward end 40 of the longitudinal slot having side walls 42 converging from the forward edge of the sleeve towards the side walls of the slot defining width 39. In other words, the side walls define a small funnel-shaped opening 40 extending towards slot 35 for ease of locating the locking tab 22 within slot 35 a blade guard 20 is initially assembled onto microsurgical knife 10' for locking into the blade covering position.

The length of longitudinal slot 35 is preferably greater than the distance 47 between the rear edge of locking tab 22 and cutting blade 14. Thereby, when tab 22 is locked within notch 37, as depicted in FIG. 2, blade 14 is not only radially surrounded by blade guard 20 but is also protected in its forward direction by virtue of cylindrical sleeve 25 extending forwardly of the blade.

As sleeve 25 slides into the blade covering position of FIG. 2, locking tab 22 reaches the terminal end of slot 35 whereupon it is in opposition to locking notch 37. With reference to FIGS. 2 and 3, locking notch 37 is actually formed with a first portion 50 immediately adjacent the terminal end of slot 35, and a second portion 52 into which tab 22 locks by slight rotation of the cylindrical sleeve to circumferentially advance the tab into the notch 37. The first and second portions 50, 52 share a common rear wall 54. As depicted in FIG. 3, first notch portion 50 has a forward wall 57 projecting rearwardly towards the rear wall to define an inlet opening of a length which may be slightly less than length L of locking tab 22. This length is slightly less than the length of second notch portion 52; the latter is slightly greater than or equal to length L of tab 22.

Due to the normal yieldability of the plastic material and the relative lengths of the parts discussed supra, slight circumferential rotation of blade guard 20 causes locking tab 22 to slip through the first notch portion 50 where it is locked into second notch portion 52 in the manner described above by riding over the locking wall or projection 57. Thus, blade guard 20 protects cutting blade 14 by simple rotation of sleeve 25. Reverse rotation of sleeve 25 allows locking tab 22 to re-enter the terminal end of longitudinal slot 35 permitting easy removal of the sleeve from the knife 10' when introduced to the sterile field.

A pair of diametrically opposed tabs 75 project radially outward from the rear end of cylindrical sleeve 25 to prevent the knife 10' from rolling when on a Mayo stand (not shown).

It will of course be understood by those skilled in the art that the particular embodiment of the invention here presented is by way of illustration only and is not meant to be restrictive. Therefore, numerous changes and modifications may be made, and the full use of equivalents may be resorted to without departing from the spirit or scope of the invention as defined in the appended claims.

What is claimed is:

1. A blade protective arrangement comprising, in combination:

a microsurgical knife including an elongate knife body, a cutting blade extending from a forward end of the knife body and a sleeve slidably received around said knife body and formed with a bore therethrough for receiving the knife body; and means for locking said sleeve to said knife body in a blade covering position, said locking means including a locking tab means formed on the knife body in the forward end thereof and a longitudinal slot extending from a front portion of the sleeve and including a terminal end and a notch extending circumferentially from the terminal end of the slot, said sleeve including an inner diameter and a forward opening dimensioned in relation to the outer diameter of the knife body and the height of the tab, for mounting in protective locking engagement with said knife body by inserting the rear end of the knife body through the forward opening in the front portion of the sleeve and sliding the sleeve towards the forward end so that the locking tab engages the slot and thereupon the terminal end thereof, and rotating the sleeve so that said tab enters the locking notch, said locking tab means being the sole locking structure provided on the knife body and said sleeve being removable by sliding it towards and off of the rear end of the knife body, said sleeve being lockable on said body only in a position engaging said locking tab means.

2. The arrangement of claim 1, wherein an inlet opening of the longitudinal slot formed on the edge of the sleeve front portion is funnel-shaped in cross-sectional plan view.

3. The arrangement of claim 1, wherein said locking tab has a major dimension extending longitudinally along the knife body to define a predetermined length of said tab.

4. The arrangement of claim 3, wherein said circumferential notch has first and second portions, said first portion located immediately adjacent the terminal end of the slot and defining an inlet into the second portion, said first portion having a length or longitudinal opening slightly less than the predetermined length of said tab so that a normal yieldability of said tab allows same to travel through the first portion into the second notch portion for locking contact.

5. The arrangement of claim 1, further including a plurality of longitudinal ribs formed on the inner surface of the sleeve for sliding contact with the exterior surface of the knife body.

6. The arrangement of claim 5, wherein said ribs extend along a rear portion of said sleeve.

7. The arrangement of claim 1, further including at least one stabilizing projection projecting radially outward from an outer surface of said sleeve to prevent rolling movement of said knife when on a Mayo stand.

8. The arrangement of claim 7, wherein said projection projects radially outward from a rear end of the sleeve.

* * * * *